/

US008332024B2

(12) United States Patent
Rapoport et al.

(10) Patent No.: US 8,332,024 B2
(45) Date of Patent: Dec. 11, 2012

(54) LOW-POWER ANALOG ARCHITECTURE FOR BRAIN-MACHINE INTERFACES

(75) Inventors: Benjamin I. Rapoport, New York, NY (US); Rahul Sarpeshkar, Arlington, MA (US); Woradorn Wattanapanitch, Cambridge, MA (US); Soumyajit Mandal, Cambridge, MA (US); Scott Arfin, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1014 days.

(21) Appl. No.: 12/127,497

(22) Filed: May 27, 2008

(65) Prior Publication Data
US 2008/0294062 A1    Nov. 27, 2008

Related U.S. Application Data

(60) Provisional application No. 60/940,149, filed on May 25, 2007, provisional application No. 60/940,105, filed on May 25, 2007, provisional application No. 60/940,103, filed on May 25, 2007.

(51) Int. Cl.
*A61B 5/04*    (2006.01)
*H03F 3/45*    (2006.01)
(52) U.S. Cl. ........................................ 600/544; 330/261
(58) Field of Classification Search .......... 600/300–301, 600/544–545; 706/15–44; 330/257–261
See application file for complete search history.

(56) References Cited

U.S. PATENT DOCUMENTS
2006/0189881 A1 * 8/2006 Fassio ........................... 600/544

FOREIGN PATENT DOCUMENTS
WO    2006076164    7/2006
WO    2006096135    9/2006

OTHER PUBLICATIONS

Baldi, Pierre. "Gradient Descent Learning Algorithm Overview: A General Dynamical Systems Perspective." IEEE Transaction on Neural Networks. vol. 6, No. 1 Jan. 1995. pp. 182-195.*
Hamici, et al. "A High-Efficiency Biotelemetry System for Implanted Electronic Device." IEEE-EMBC and CMBEC. Theme 7: Instrumentation. 1995.*
Irazoqui-Pastor et al., "In-Vivo EEG Recording Using a Wireless Implantable Neural Transceiver" Conference Proceedings 1st International IEEE EMBS Conference on Neural Engineering 2003 (CAT. No. 03EX606, IEEE Piscataway, NJ, USA, 2003, pp. 622-625.
Harrison et al., "A Low-Power Integrated Circuit for a Wireless 100-Electrode Neural Recording System" ISSCC 2006/Session 30/Silicon for Biology 30.2, 2006 IEEE International Solid-State Circuits Conference, pp. 554-555 & 672.
"Cognitive Control Signals for Neural Prosthetics," Musallam et al. Science. Jul. 9, 2004. vol. 305, p. 258-262.

(Continued)

*Primary Examiner* — Patricia Mallari
*Assistant Examiner* — Tiffany Weston
(74) *Attorney, Agent, or Firm* — Gesmer Updegrove LLP

(57) ABSTRACT

An ultra-low-power circuit for wireless neural recording and stimulation is provided. The circuit includes a neural amplifier with adaptive power biasing for use in multi-electrode arrays and a decoding and/or learning architecture. An impedance-modulation telemetry system provides low-power data telemetry. Also, the circuit includes a wireless link for efficient power transfer, and at least one circuit for wireless stimulation of neurons.

24 Claims, 15 Drawing Sheets

OTHER PUBLICATIONS

"Neuronal Ensemble Control of Prosthetic Devices, by a Human with Tetraplegia," Hochberg et al. Nature. Jul. 13, 2006. vol. 442, p. 164-171.

"Neuronal Ensemble Control of Prosthetic Devices by a Human with Tetraplegia," Hochberg et al. Nature. Jul. 13, 2006. (Supplementary Information). p. 1-6.

"Bayesian Population Decoding of Motor Cortical Activity Using a Kalman Filter," Wu et al. Neural Computation, Massachusetts Institute of Technology. May 3, 2005. vol. 18, p. 80-118.

"A Low-Power Integrated Circuit for a Wireless 100-Electrode Neural Recording System," Harrison et al. IEEE Journal of Solid-State Circuits. Jan. 2007. vol. 42, No. 1, p. 123-133.

"An Ultra-Low-Power Programmable Analog Bionic Ear Processor," Sarpeshkar et al. IEEE Transactions on Biomedical Engineering. Apr. 2005. vol. 52, No. 4, p. 711-727.

"An Analog Bionic Ear Processor with Zero-Crossing Detection," Sarpeshkar et al. Proceedings of the IEEE International Solid State Circuits Conference. Paper 4.2, p. 78-79, San Francisco, CA, Feb. 2005.

"A Low-Power Wide Dynamic Range Envelope Detector," Zhak et al. IEEE Journal of Solid-State Circuits. Oct. 2003. vol. 38, No. 10, p. 1750-1753.

"A 10-nW 12-bit Accurate Analog Storage Cell With 10-aA Leakage," O'Halloran et al. IEEE Journal of Solid-State Circuits. Nov. 2004. vol. 39, No. 11, p. 1985-1996.

"Feedback Analysis and Design of RF Power Links for Low-Power Bionic Systems," Baker et al. Transactions on Biomedical Circuits and Systems. Apr. 2007. vol. 1, No. 1., p. 1-10.

"An Analog Storage Cell with 5e-/sec Leakage," O'Halloran et al. Research Lab of Electronics, Massachusetts Institute of Technology. IEEE 2006. ISCAS. p. 557-560.

"Brain-Controlled Interfaces Movement Restoration with Neural Prosthetics," Schwartz et al. Neuron. Oct. 5, 2006. vol. 52., p. 205-220.

"A Low-Power Low-Noise CMOS Amplifier for Neural Recording Applications," Harrison et al. IEEE Journal of Solid-State Circuits. Jun. 2003. vol. 38, No. 6, p. 958-965.

"A Wideband Frequency-Shift Keying Wireless Link for Inductively Powered Biomedical Implants," Ghovanloo et al. IEEE Transactions on Circuits and Systems. Dec. 2004. vol. 51, No. 12., p. 2374-2383.

"Low-Power Circuits for Brain-Machine Interfaces," Sarpeshkar et al. Massachusetts Institute of Technology & Division of Biology, California Institute of Technology. IEEE 2007. p. 2068-2071.

"A Sub-Microwatt Low-Noise Amplifier for Neural Recording," Holleman et al. Department of Electrical Engineering, University of Washington.

"Identification of a Forebrain Motor Programming Network for the Learned Song of Zebra Finches," Vu et al. The Journal of Neuroscience. Nov. 1994. vol. 14, No. 11, p. 6924-6934.

"Ensemble Coding of Vocal Control in Birdsong," Leonardo et al. The Journal of Neuroscience. Jan. 19, 2005. vol. 25, No. 3, p. 652-661.

"Stimulus-Artifact Elimination in Multi-Electrode System," Brown et al. IEEE Transactions on Biomedical Circuits and Systems. Mar. 2008. vol. 2, No. 1, p. 10-21.

"An Integrated System for Simultaneous, Multichannel Neuronal Stimulation and Recording," Blum et al. IEEE Transactions on Circuits and Systems-1 Regular Papers. Dec. 2007. vol. 54, No. 12, p. 2608-2618.

"Low-Power Circuits for Brain-Machine Interfaces," Sarpeshkar et al., IEEE Transactions on Biomedical Circuits and Systems. 2008.

"An Energy-Efficient Micropower Neural Recording Amplifier," Wattanapanitch et al. IEEE Transactions on Biomedical Circuits and Systems. Jun. 2007. vol. 1, No. 2, p. 136-147.

"Brain-Machine Interfaces past, present, and future," Lebedev et al. Trends in Neuroscience. www.sciencedirect.com. Jul. 21, 2006. vol. 29, No. 9.

"Wireless Multichannel Biopotential Recording Using an Integrated FM Telemetry Circuit," Mohseni et al. IEEE Transactions on Neural Systems and Rehabilitation Engineering. Sep. 2005. vol. 13, No. 3, p. 263-271.

"A Wide-Band Power-Efficient Inductive Wireless Link for Implantable Microelectronic Devices Using Multiple Carriers," Ghovanloo et al. IEEE Transactions on Circuits and Systems 1—: Regular Papers. Oct. 2007. vol. 54, No. 10, p. 2211-2221.

"A Three-Dimensional Neural Recording Microsystem With Implantable Data Compression Circuitry," IEEE Journal of Solid-State Circuits. Dec. 2005. vol. 40, No. 12, p. 2796-2804.

"A Bidirectional Wireless Link for Neural Prostheses that Minimizes Implanted Power Consumption." Mandal et al. Department of Electrical Engineering and Computer Science, Massachusetts Institute of Technology. 2007 IEEE. p. 45-48.

"A Fully Integrated Low-Power BPSK Demodulator for Implantable Medical Devices," Hu et al. IEEE Transactions on Circuits and Systems—1: Regular Papers. Dec. 2005. vol. 52, No. 12., p. 2552-2562.

"Closed-Loop Class E Transcutaneous Power and Data Link for MicroImplants," Troyk et al. IEEE Transactions on Biomedical Engineering. Jun. 1992. vol. 39, No. 6., p. 589-599.

"A CMOS Micro-power Wideband Data/Power Transfer System for Biomedical Implants," Omeni et al. Department of Electrical and Electronics Engineering, Imperial College London. 2003 IEEE. p. V-61: V-64.

"Design and Analysis of an Adaptive Transcutaneous Power Telemetry for Biomedical Implants," Wang et al. IEEE Transactions on Circuits and Systems—1: Regular Papers. Oct. 2005. vol. 52, No. 10., p. 2109-2117.

"Minimally Invasive Retinal Prosthesis," Theogarajan et al. IEEE International Solid-State Circuits Conference/ 2006/ Session 2/ Biomedical Systems/2.

"A Low-Power Asynchronous Interleaved Sampling Algorithm for Cochlear Implants that Encodes Envelope and Phase Information," Sit et al. IEEE Transactions on Biomedical Engineering. Jan. 2007. vol. 54, No. 1, p. 138-149.

"A Power-Efficient Voltage-Based Neural Tissue Stimulator with Energy Recovery," Kelly et al. IEEE International Solid-State Circuits Conference/2004/Session 12/ Biomicrosystems/12.6.

"A Low-Power Blocking-Capacitor-Free Charge-Balanced Electrode-Stimulator Chip with Less than 6 nA DC Error for 1-mA Full-Scale Stimulation," Sit et al. IEEE Transactions on Biomedical Circuits and Systems. Sep. 2007. vol. 1, No. 3, p. 172-183.

"A Cochlear Implant Processor for Encoding Music and Lowering Stimulation Power," Sit et al. IEEE Pervasive Computing. 2008. p. 40-48.

\* cited by examiner

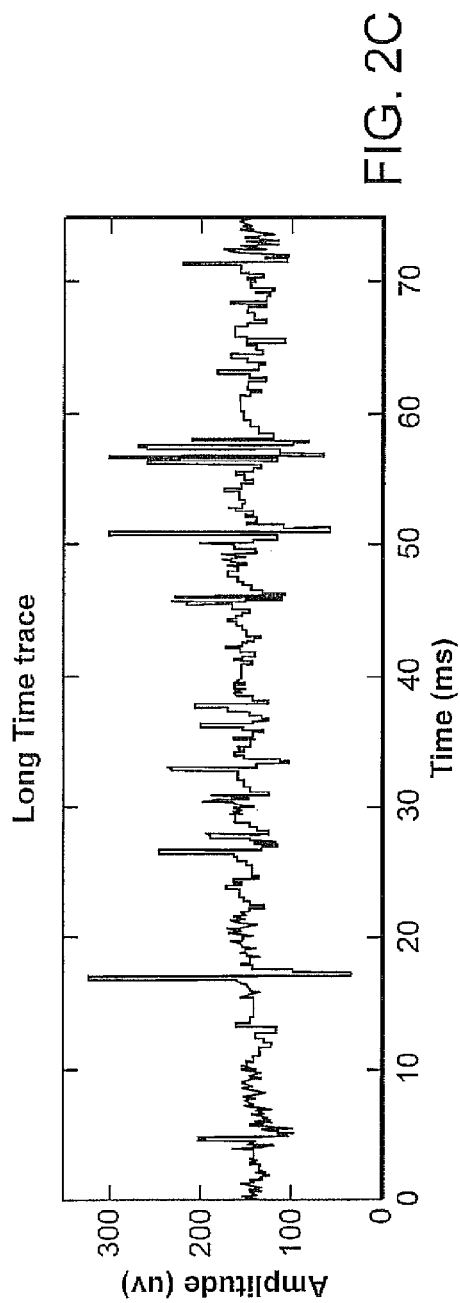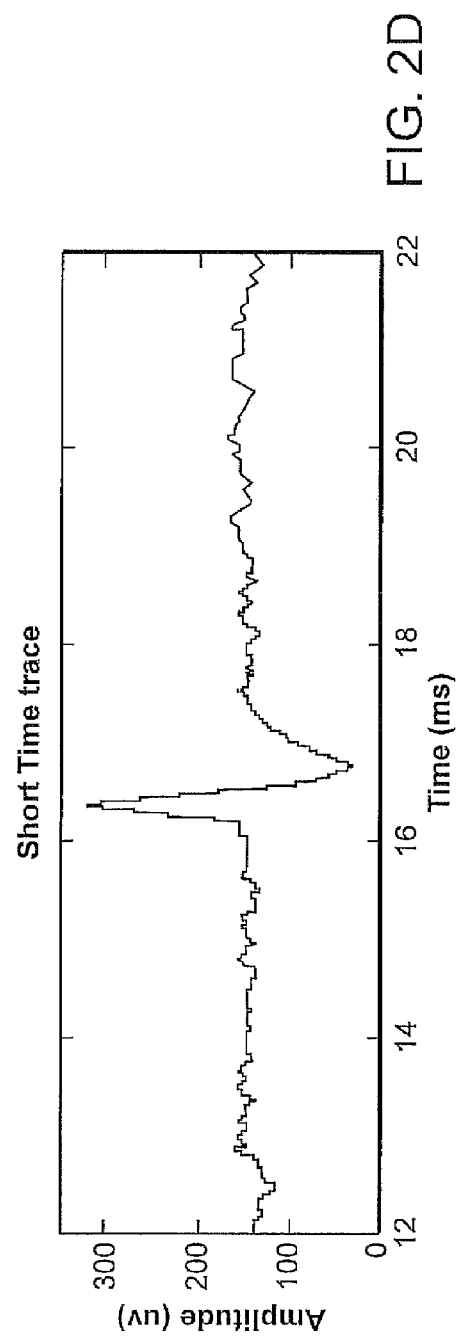

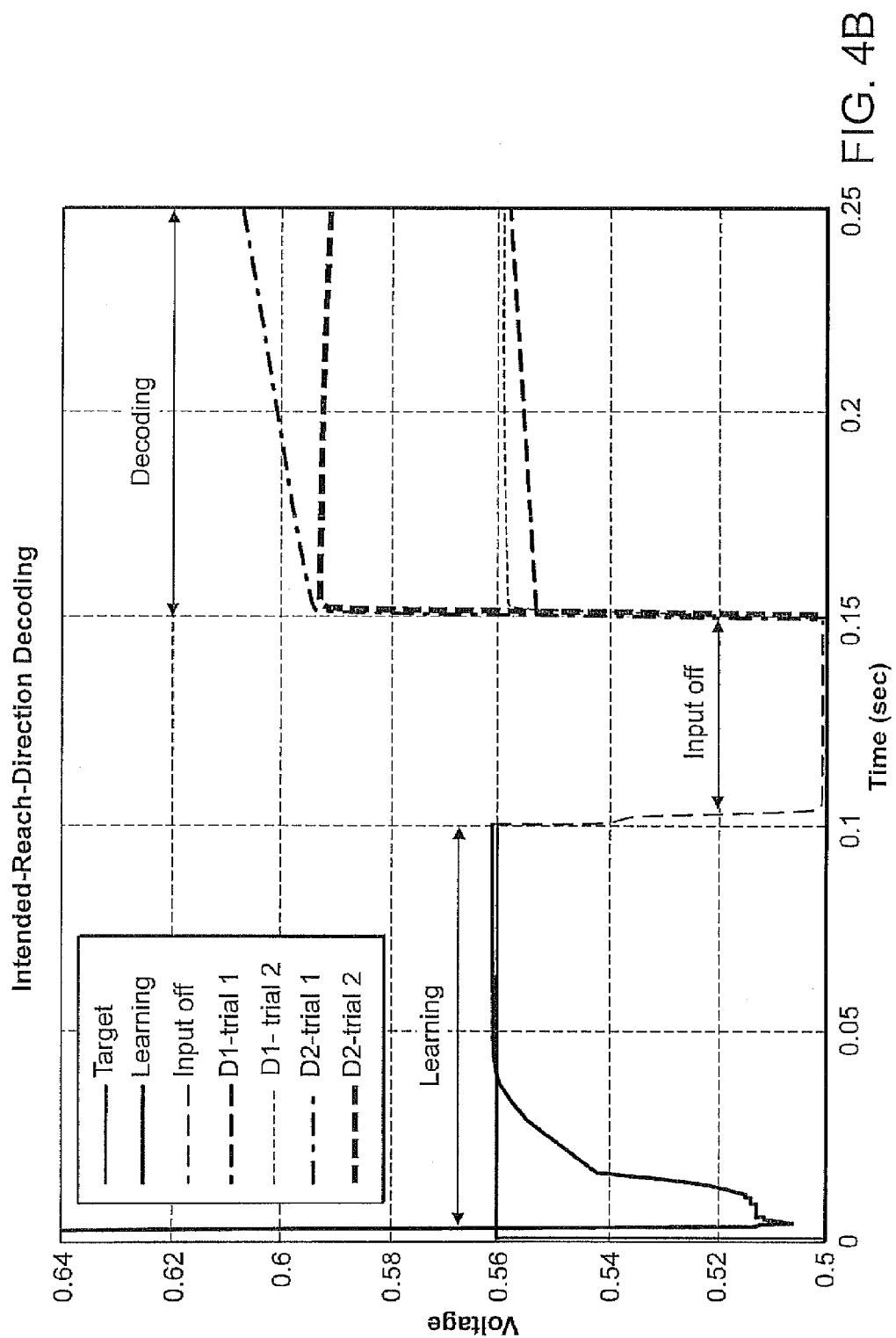

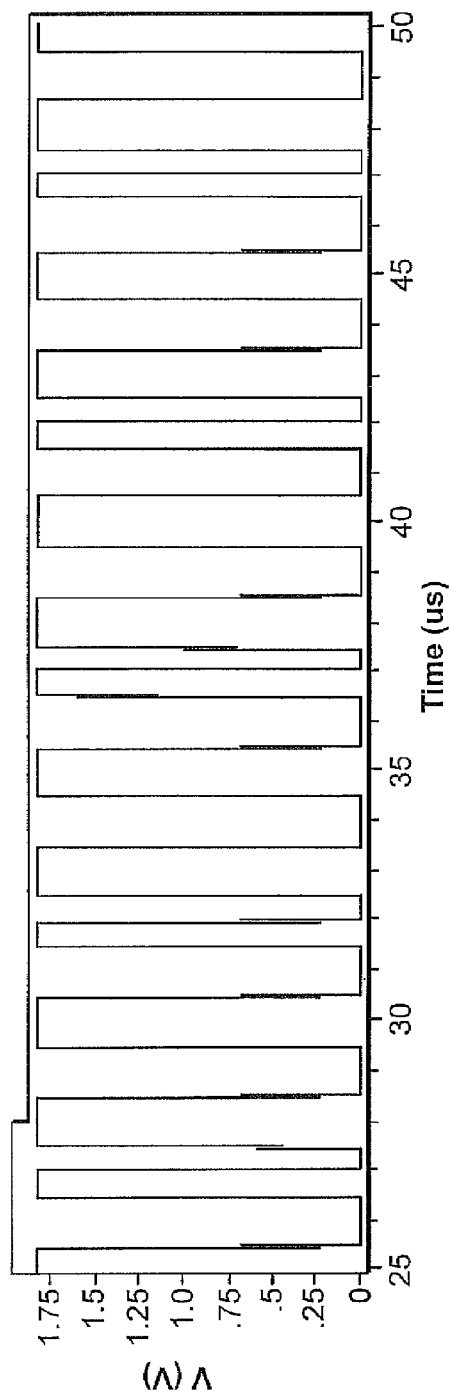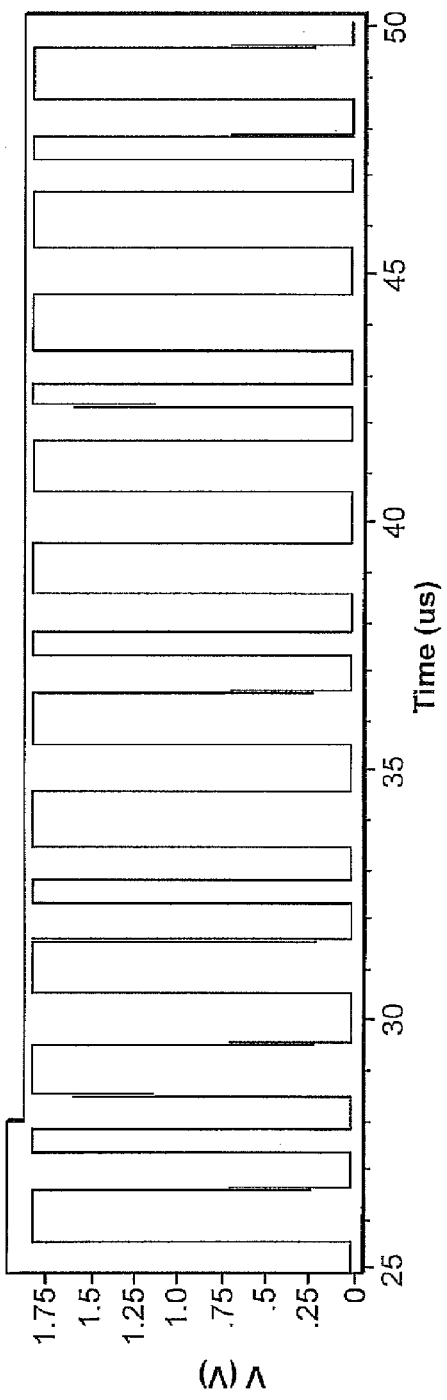

LOW-POWER ANALOG ARCHITECTURE FOR BRAIN-MACHINE INTERFACES

PRIORITY INFORMATION

This application claims priority from provisional application Ser. No. 60/940,149 filed May 25, 2007, provisional application Ser. No. 60/940,105 filed May 25, 2007, and provisional application Ser. No. 60/940,103 filed May 25, 2007, all of which are incorporated herein by reference in their entireties.

This invention was made with government support awarded by the National Science Foundation under Contract Number DGE-0645960. The government has certain rights in the invention.

BACKGROUND OF THE INVENTION

The invention is related to the field of brain machine interfaces (BMIs), and in particular to ultra-low-power circuits for brain-machine interfaces.

Large-scale chronic multi-electrode neural recording systems have emerged as an important experimental paradigm for investigating brain function. Experiments using such Brain-Machine Interfaces (BMIs) have shown that it is possible to predict intended limb movements by analyzing simultaneous recordings from many neurons. These findings have suggested a potential approach for treating paralysis. Chronic use of BMIs with large numbers of electrodes limits having a BMI where the system is miniature and implantable, heat dissipated in the brain is minimized, and frequent battery replacement and resurgery in implanted systems is unnecessary.

SUMMARY OF THE INVENTION

According to one aspect of the invention, there is provided an ultra-low-power circuit for wireless neural recording and stimulation. The circuit includes a neural amplifier with adaptive power biasing for use in multi-electrode arrays and a decoding and/or learning architecture. An impedance-modulation telemetry system provides low-power data telemetry. Also, the circuit includes a wireless link for efficient power transfer, and at least one circuit for wireless stimulation of neurons.

According to another aspect of the invention, there is provided an ultra-low-power circuit for wireless neural recording and stimulation. The circuit includes a neural amplifier with adaptive power biasing for use in multi-electrode arrays. The neural amplifier having a gain stage implemented using an all-subthreshold and folded-cascode architecture and a bandwidth limiting stage to maintain a constant overall bandwidth and vary the gain stage's bias current to adapt its noise per unit bandwidth. A decoding and/or learning architecture performs data compression. The decoding and/or learning architecture is implemented using a gradient descent algorithm to learn a decoding filter via supervised learning. An impedance-modulation telemetry system performs low-power data telemetry. The impedance-modulation telemetry system includes an external unit broadcasting a continuous wave carrier using a class-E amplifier topology; and an implanted unit that switches its impedance from minimum, a series resonant coil, to a maximum, an open-circuited coil by using a switch in series with a capacitor to amplitude modulate a load at the primary. Also, the circuit includes a wireless link for efficient power transfer, and at least one circuit for wireless stimulation of neurons.

According to another aspect of the invention, there is provided a method of implementing an ultra-low-power circuit for wireless neural recording and stimulation. The method includes providing a micropower neural amplifier with adaptive power biasing for use in multi-electrode arrays, and providing a decoding and/or learning architecture for data compression. An impedance-modulation telemetry system is provided low-power data telemetry. Furthermore, the method includes providing a wireless link for efficient power transfer and providing at least one circuit for wireless stimulation of neurons.

According to another aspect of the invention, there is provided a method of performing the operations of an ultra-low-power circuit for wireless neural recording and stimulation. The method includes performing adaptive power biasing for use in multi-electrode arrays. The neural amplifier having a gain stage implemented using an all-subthreshold and folded-cascode architecture and a bandwidth limiting stage to maintain a constant overall bandwidth and vary the gain stage's bias current to adapt its noise per unit bandwidth. Also, the method includes compressing data using a continuous-time analog gradient descent algorithm to learn a decoding filter via supervised learning. A low-power data telemetry is performed using an impedance-modulation telemetry system comprising an external unit broadcasting a continuous wave carrier using a class-E amplifier topology; and an implanted unit that switches its impedance from minimum, a series resonant coil, to a maximum, an open-circuited coil by using a switch in series with a capacitor to amplitude modulate a load at the primary. In addition, the method includes transferring power using wireless link, and wirelessly stimulating neurons.

According to another aspect of the invention, there is provided an ultra-low-power microelectronic system for wireless neural recording capable of being completely implanted in the brain. The ultra-low-power microelectronic system includes a plurality of neural amplifiers with adaptive power biasing used in multi-electrode arrays and a decoding architecture. An impedance-modulation telemetry system is provided for low-power data telemetry. A wireless link provides efficient power transfer.

BRIEF DESCRIPTION OF THE DRAWINGS

FIGS. 2C-2D are graphs illustrating recording information obtained from the RA region of a zebra finch brain using the amplifier circuit shown;

FIG. 4B is a graph indicating that the architecture successfully learns and decodes from spiking data in a monkey;

FIGS. 5B-5C are graphs demonstrating the successful transmission of data by the RF data telemetry design;

DETAILED DESCRIPTION OF THE INVENTION

Figure 1:
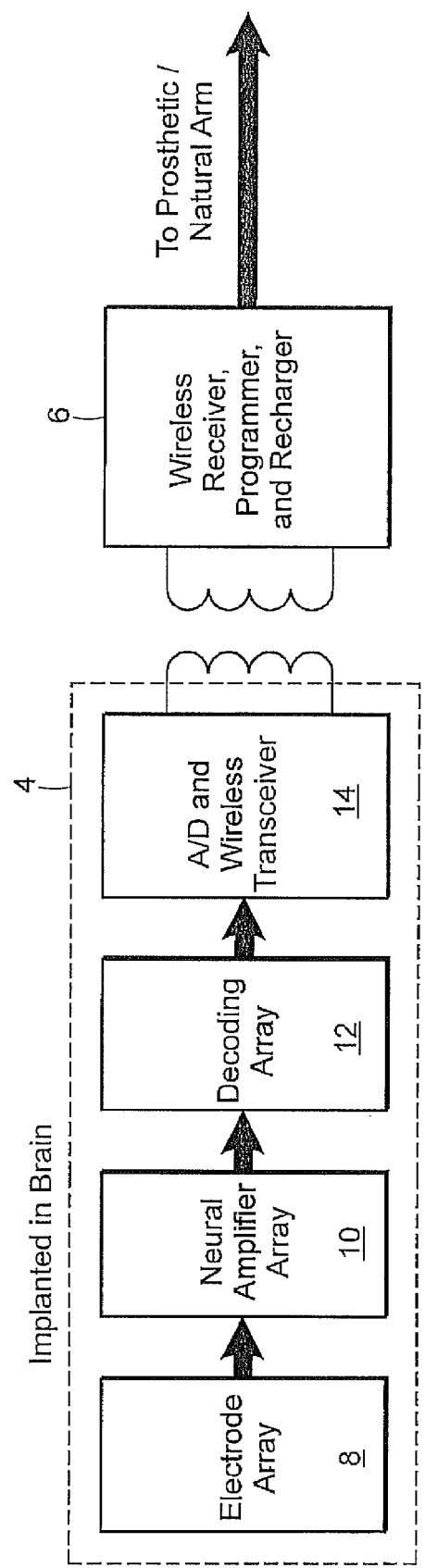
FIG. 1 shows a block diagram illustrating the components used in the operation of the invention.

The invention involves ultra-low-power circuits for brain-machine interfaces with applications with application for prosthetics for paralyzed individuals, amputees, and the blind; brain implantable devices for those with Parkinsonism, Parkinson's disease, epilepsy, and other disorders of the brain, as well as experimental neuroscience systems. FIG. 1 shows a block diagram 2 illustrating the components used in the operation of the invention. The invention includes an implanted portion 4 and external portion 6. The implanted portion 4 includes electrode arrays 8 having a die size of a single chip with a 10×10 array of electrodes spaced apart by 400 μm is 4 mm×4 mm=16 mm², however in other embodiments the die size can vary. The implanted portion 4 also includes a micropower neural amplifier 10 with adaptive power biasing for use in multi-electrode arrays 8, an analog linear decoding and learning array 12 for data compression 8, and a radio-frequency (RF) telemetry component 14 for impedance modulation for low-power data telemetry. The external portion 6 includes a wireless receiver link for efficient power transfer; mixed-signal system integration for efficiency, robustness, and programmability; and circuits for wireless stimulation of neurons, as shown in FIG. 1. Experimental results from chips that have recorded from and stimulated neurons in the zebra-finch brain and from RF power-link systems are presented.

Low-power neural amplifiers are extremely important in such interfaces since one such amplifier is needed for each electrode. The invention uses a micropower neural amplifier that appears to be the most power-efficient neural amplifier reported to date. The invention provides a technique for adapting the noise floor of this amplifier to the noise-floor requirements at each recording site, potentially enabling multi-electrode systems to reduce recording power by an order of magnitude.

RF data telemetry component 14 is necessary to communicate information wirelessly from neurons in the brain through the skull and skin. Due to the relatively high power costs of transcutaneous data communication (100 electrodes with 12-bit 20 kHz-sampled neural information yield a data rate of 24 Mbs$^{-1}$), some form of data compression is needed to reduce the bandwidth of information transmitted from the brain. An adaptive, learnable, multi-input-multi-output linear filter that projects firing-rate neuronal data onto a few motor output parameters has successfully been used to decode movement intentions from neural signals.

Such filters have proven useful for interpreting population codes of neurons in various brain regions and perform comparably to adaptive Kalman filters and other probabilistic decoding techniques. The invention uses an analog decoding and learning component 12 to compute such a filter in a power-efficient analog fashion, thereby allowing high data compression (an output rate of 3×100 Hz×8 bits=2.4 kbs$^{-1}$ is more than sufficient for anticipated applications). Circuit simulations are presented of the architecture that successfully learn and decode a monkey's intention to move from its prerecorded neural spiking data.

The invention provides a novel low-power impedance-modulation technique for brain-machine Interfaces (BMIs) that can be used to transmit RF data from the brain flexibly and efficiently so that the power costs of communication are almost solely borne by external RF circuitry outside the skin and skull rather than by the implanted RF circuitry within, as in prior designs. Thus, heat and power dissipation in implanted hardware within the brain can be minimized.

Efficient wireless links that transmit RF power through the skin are necessary to power implanted chips in the interface directly via rectification and possibly also to recharge implanted batteries with a finite number of recharges. The invention presents data from an RF link that achieves efficiencies near theoretical limits and summarizes the tradeoffs needed to make such links efficient.

Figure 2A:
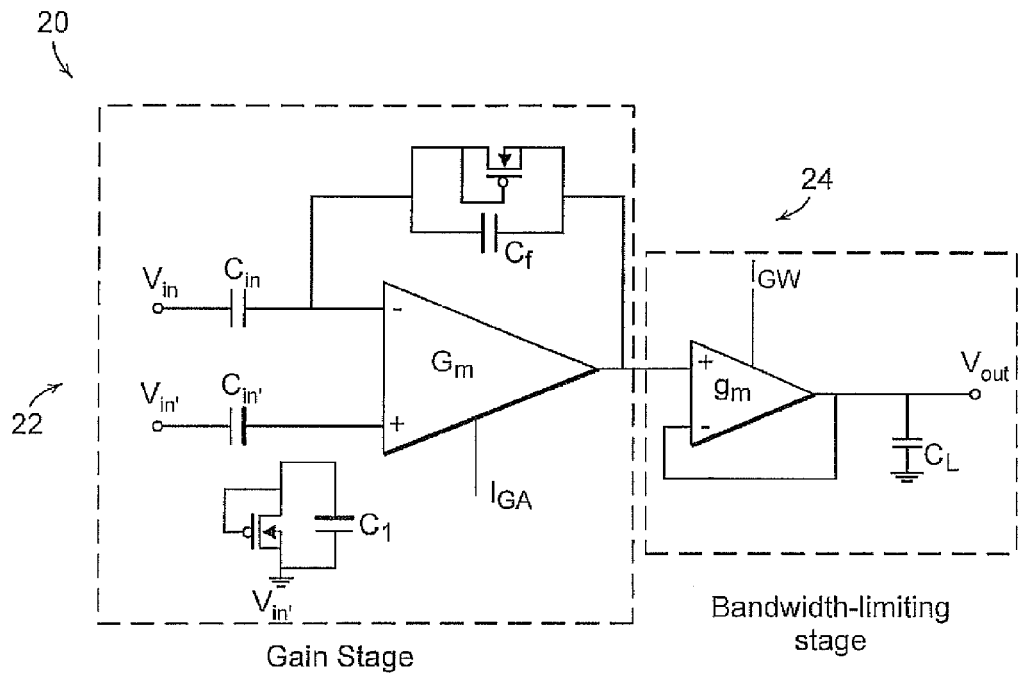
FIGS. 2A-2B are schematic diagrams illustrating the adaptive micropower neural amplifier circuit used in accordance with the invention.
Figure 2B:
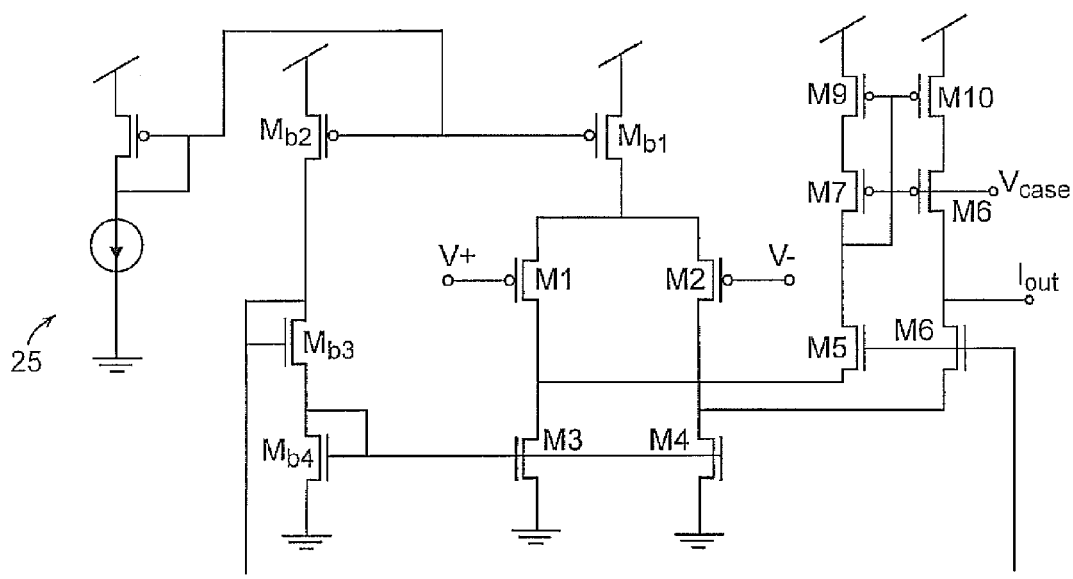

FIG. 2A shows the architecture of the adaptive micropower amplifier 20. The micropower amplifier 20 is similar to the amplifier structure as disclosed in U.S. Provisional Ser. No. 60/940,105 filed May 25, 2007, and filed as U.S. patent application Ser. No. 12/127,497, filed on even date herewith, the disclosures of which is hereby incorporated by reference in their entireties. The first gain stage 22 is implemented with the use of an all-subthreshold and folded-cascode architecture 25 shown in FIG. 2B, allowing low-voltage operation. One can add a bandwidth-limiting stage 24 to keep the overall bandwidth constant as one can vary the bias current of the gain stage 22 to adapt its noise per unit bandwidth. The additional power of the bandwidth-limiting stage 22 is negligible because the 100× gain provided by the gain stage alleviates its noise floor requirements. FIGS. 2C-2D shows data recorded from the RA region of a zebra-finch bird brain with a Carbostar 800 kohm impedance electrode and the amplifier. There was no discernible difference compared with a recording from a commercial neural amplifier. An input-referred noise of 5.5 μV rms is measured over a 5 kHz bandwidth (integrated from 0.5 Hz-5 kHz) with a power consumption of 7 μW for 40 dB of gain.

Although the amplifier's current consumption normalized for bandwidth and noise is about 1.3× larger than that of the best prior design. The power consumption is 0.52× lower because the topology permits 2V rather than 5V operation. In prior designs, the 5V power supply was necessary for maintaining large overdrive voltages in some above-threshold transistors to minimize their noise contributions. The amplifier occupies a chip area of 0.09 mm² and was fabricated in a commercial 0.5 μm CMOS process.

The power required to build an amplifier with constant bandwidth, constant power-supply voltage, and an input-referred noise $v_n$ scales as $1/v_n^2$ if the amplifier is thermal noise limited. This relation clearly shows the steep power cost of achieving low-noise performance in an amplifier. Neural amplifiers have been designed to handle the worst-case range of signal strengths that may be expected in any recording situation. In practice, there is considerable variance in the noise and action potential strengths of typical recordings. The steep cost of achieving low-noise performance in an amplifier suggests that rather than designing amplifiers with the lowest noise at all locations, significant power savings can be achieved if an amplifier can adapt its input-referred noise to the local noise floor.

Figure 4A:
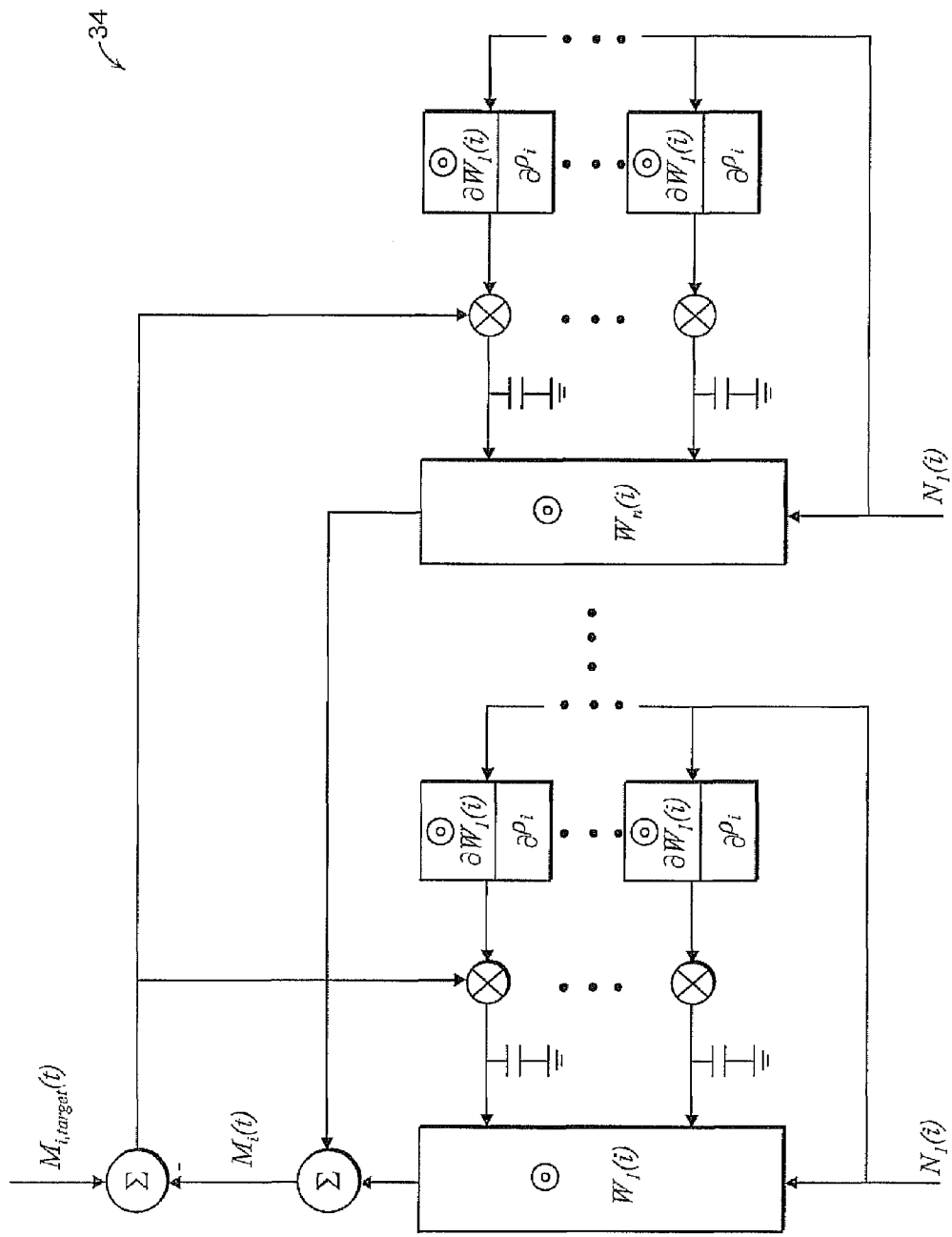
FIG. 4A is schematic diagram of an analog architecture for linear decoding and learning.

This adaptability enables the overall power in a multi-electrode system to be determined by the average electrode rather than by the worst-case electrode. The control loop for setting each amplifier's bias current in a multi-electrode array may easily be implemented with little power overhead per recording site: One very-low-noise neural amplifier is used infrequently to evaluate the noise floor at each recording site in a sequential and multiplexed fashion so that its power overhead is shared amongst all recording sites and it is only active during calibration as shown in FIG. 4A.

Figure 3A:
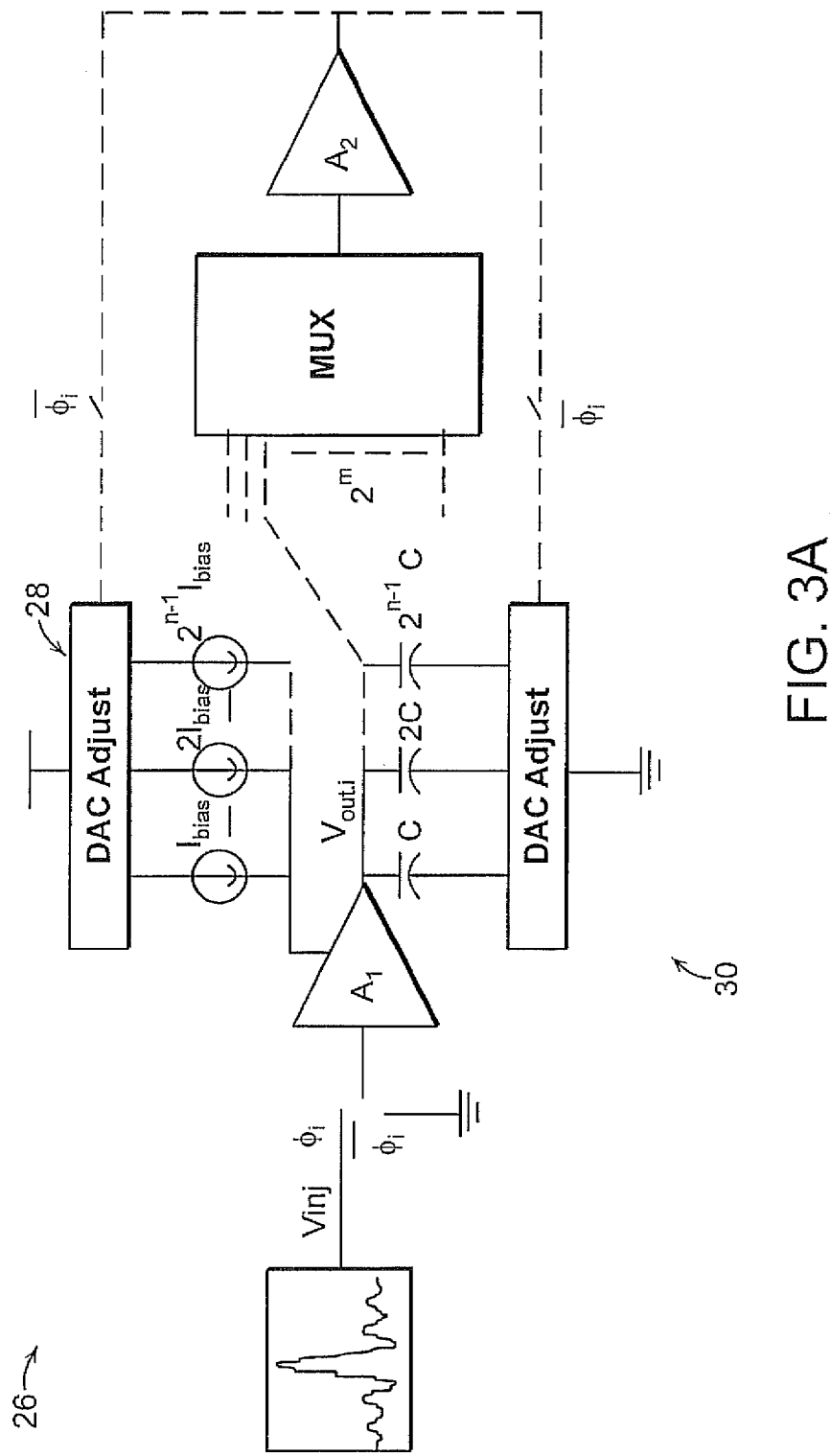
FIG. 3A is a schematic diagram illustrating an adaptive technique for neural amplifier biasing.

In particular FIG. 3A shows a circuit 26 used in adaptive biasing. A local recording amplifier $A_1$ has digital-to-analog converter (DACs) 28, 30 that can simultaneously vary its bias current(s) (Iout-$2^{n-1}$Iout) and its output capacitance(s) (C-$2^{n-1}$C) such that its bandwidth remains constant while its input-referred noise decreases. Higher capacitances (C-$2^{n-1}$C) and bias currents (Iout-$2^{n-1}$Iout) correspond to lower noise and higher power consumption. Many such local recording amplifiers (Vout,j) in an array are periodically multiplexed in a multiplexer MUX onto a very low noise amplifier $A_2$ that monitors all these local amplifiers. The amplifier $A_2$ is power hungry but, since it is shared across the array and only turned on during monitoring, its power consumption is negligible: One 100 μW amplifier for an entire array of 100 electrodes (Vin,j) amounts to an increase of 1 μW per electrode if $A_2$ is constantly on. During calibration, $A_2$ compares the output noise of $A_1$ when it is connected to ground and when it is connected to its neural recording environment. It alters the DAC parameters of $A_1$ until the energy of these two noise signals over a given frequency band are in some acceptable ratio. Low power filtering and energy extraction on the output of $A_2$ with circuits as described in can extract the energy in the noise signals at the output of $A_2$. Many related techniques arising from similar principles, based on the aggregate statistics of amplifier array signals, rather than on the properties of signals recorded by individual amplifiers alone, may be devised by those skilled in the art An added benefit of this architecture is that non-functional electrodes can simply be turned off by setting their DAC currents to zero.

Figure 3B:
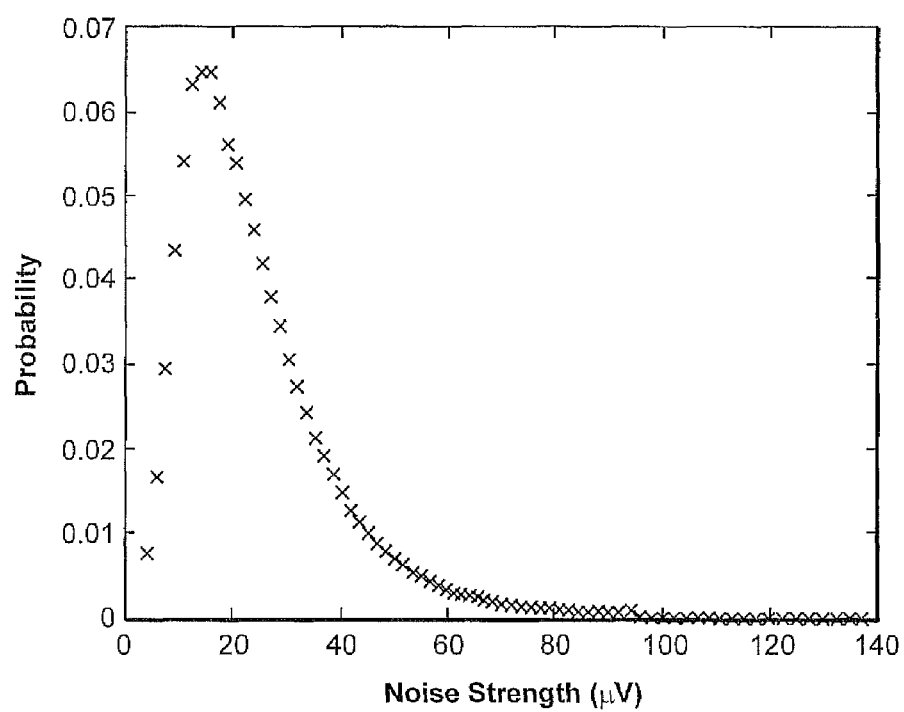
FIG. 3B is a graph illustrating the noise distribution computed by sampling statistics from a chronically-implanted array of 64 electrodes in a monkey brain.

FIG. 3B shows a typical probability distribution obtained from neural data recorded using a chronically-implanted 64-electrode array in a monkey. For this probability distribution, using the adaptive amplifiers, a 12× reduction in neural recording power for an entire system of 100 electrodes can be achieved.

In the case of a bionic-ear processor, it has been experimentally demonstrated that analog pre-processing and delayed digitization enable order-of-magnitude power reductions over traditional A-D-then-digital signal processor (DSP) implementations. Such implementations can also preserve programmability and robustness to offset, power-supply noise, and temperature variations, It was important to determine whether it may be possible to achieve similar power reductions in implementing digital linear decoding and learning algorithms with analog architectures operating on analog neuronal firing rates.

FIG. 4A shows a novel analog architecture that uses a continuous-time analog gradient descent algorithm to learn a decoding filter 34 via supervised learning. The decoding filter 34 is similar to the amplifier structure as disclosed in U.S. Provisional Ser. No. 60/940,103 filed May 25, 2007, and filed as US patent application Ser. No. 12/127,380, filed on even date herewith, the disclosures of which are hereby incorporated by reference in their entireties. Using simple transconductor-capacitor filters and multiplier, adder and subtractor circuits in subthreshold technology, it was shown show via SPICE simulations in a 0.18 μm process that the architecture is capable of learning and then decoding a monkey's intention to move its arm from data recorded from ten neurons in its posterior parietal cortex, shown in FIG. 4B.

The recorded spike-time data from a monkey were converted into analog firing rates using fourth-order wavelet-like analog matched filters on 1 ms-wide spiking inputs, followed by thresholding, followed by third-order analog interpolation filters. The figure shows that the performance is similar to that achieved via digital decoding and learning algorithms. The power consumption of a single channel is near 54 nW and a complete 100 channel system with 3 motor outputs is implementable with 17 μW using a 1V power supply on a modest-sized chip. Thus, the analog architecture is extremely power efficient and can enable a dramatic reduction in communication power due to its data-compression properties. An actual chip implementation would need overhead for offset and mismatch compensation via DAC calibration, and temperature- and power-supply-immune biasing.

Figure 5A:
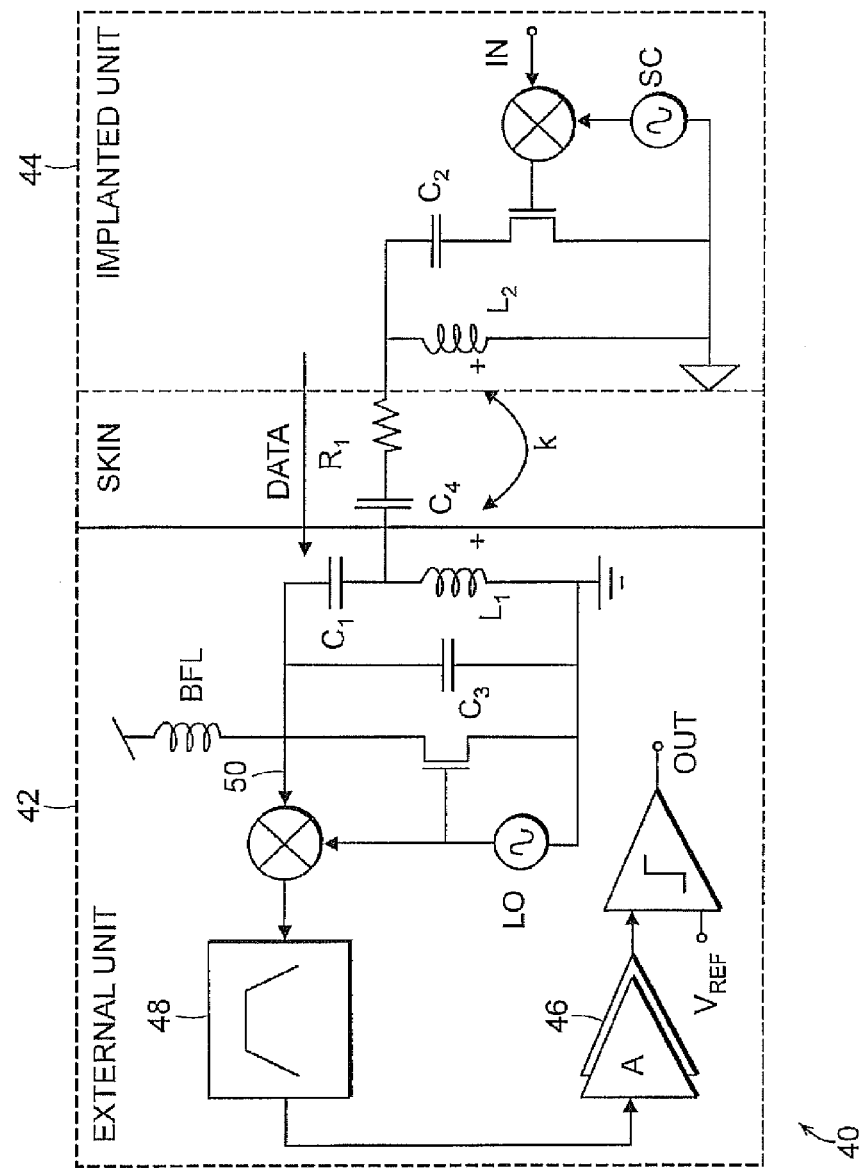
FIG. 5A is a schematic diagram illustrating a low-power RF data telemetry design using impedance modulation.

FIG. 5A shows a low-power RF data telemetry design 40 using an impedance modulation scheme. The primary external unit 42 broadcasts a 27 MHz continuous-wave carrier using a class-E amplifier topology. The secondary implanted unit 44 switches its impedance from minimum, a series resonant coil $L_2$, to maximum, an open-circuited coil $L_2$, by using a switch in series with $C_2$, thus amplitude-modulating the load at the primary unit 42. The load modulation is detected by mixing the primary voltage (LO) with the unmodulated carrier 50 and low-pass filtering 48 the output. The large carrier component, which gets mixed down to DC, is rejected by AC coupling the output of the filter 48 into a chain of amplifiers 46. The output of the amplifier chain 46 is thresholded to recover the Manchester-encoded transmitted data.

The skin is modeled having a capacitance $C_4$ and a resistance $R_1$. SPICE-based circuit simulations from a 0.18 μm process in FIGS. 5B-5C show successful data transmission at rates exceeding 1 Mbps even when a very pessimistic value of k=0.05 is assumed for the coupling factor between coils $L_1$ and $L_2$, the quality factor of the primary 42 is given by $Q_1$=10, and the quality factor of the secondary 44 is given by $Q_2$=4. Thus, the link design is robust to changes in the coupling factor and inductor quality factors. The primary 42 power consumption was found to be 1.1 mW and the secondary power consumption was found to be near zero (<1 μW). This design is not thermal-noise limited, which means that the transmitted power can be reduced further.

Figure 6A:
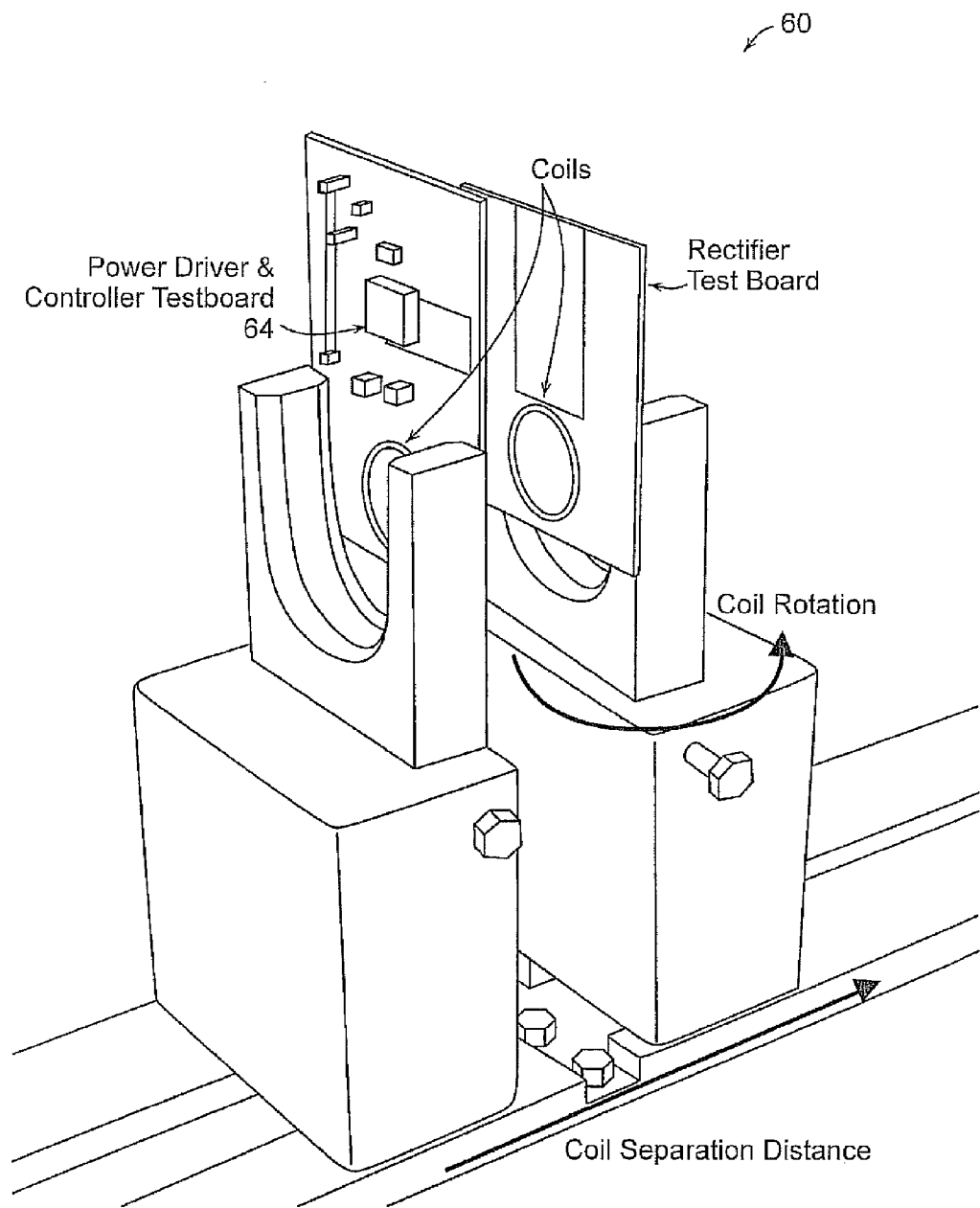
FIG. 6A is a schematic diagram of the RF power link used in accordance with the invention.
Figure 6B:
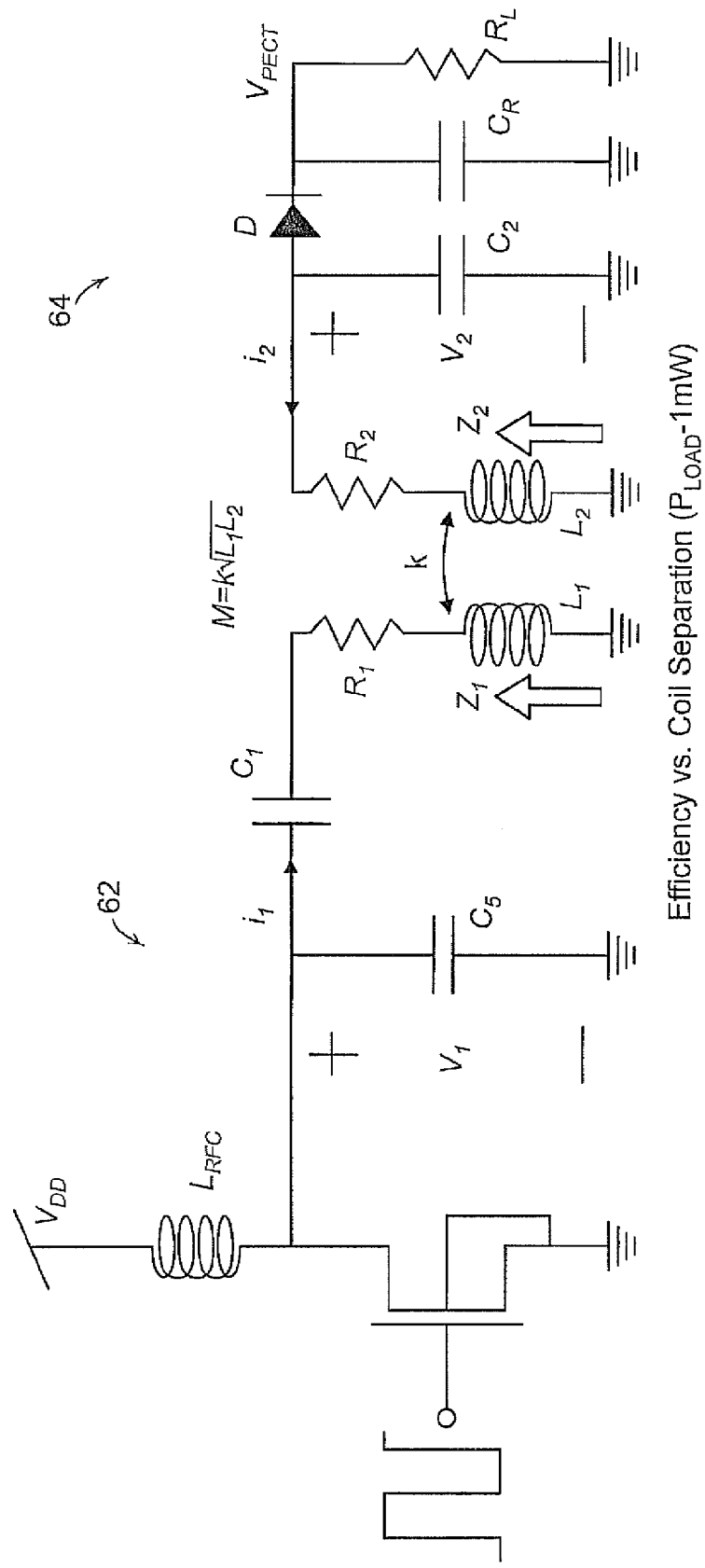
FIG. 6B is a schematic diagram illustrating the RF power link circuits and rectifier.
Figure 6C:
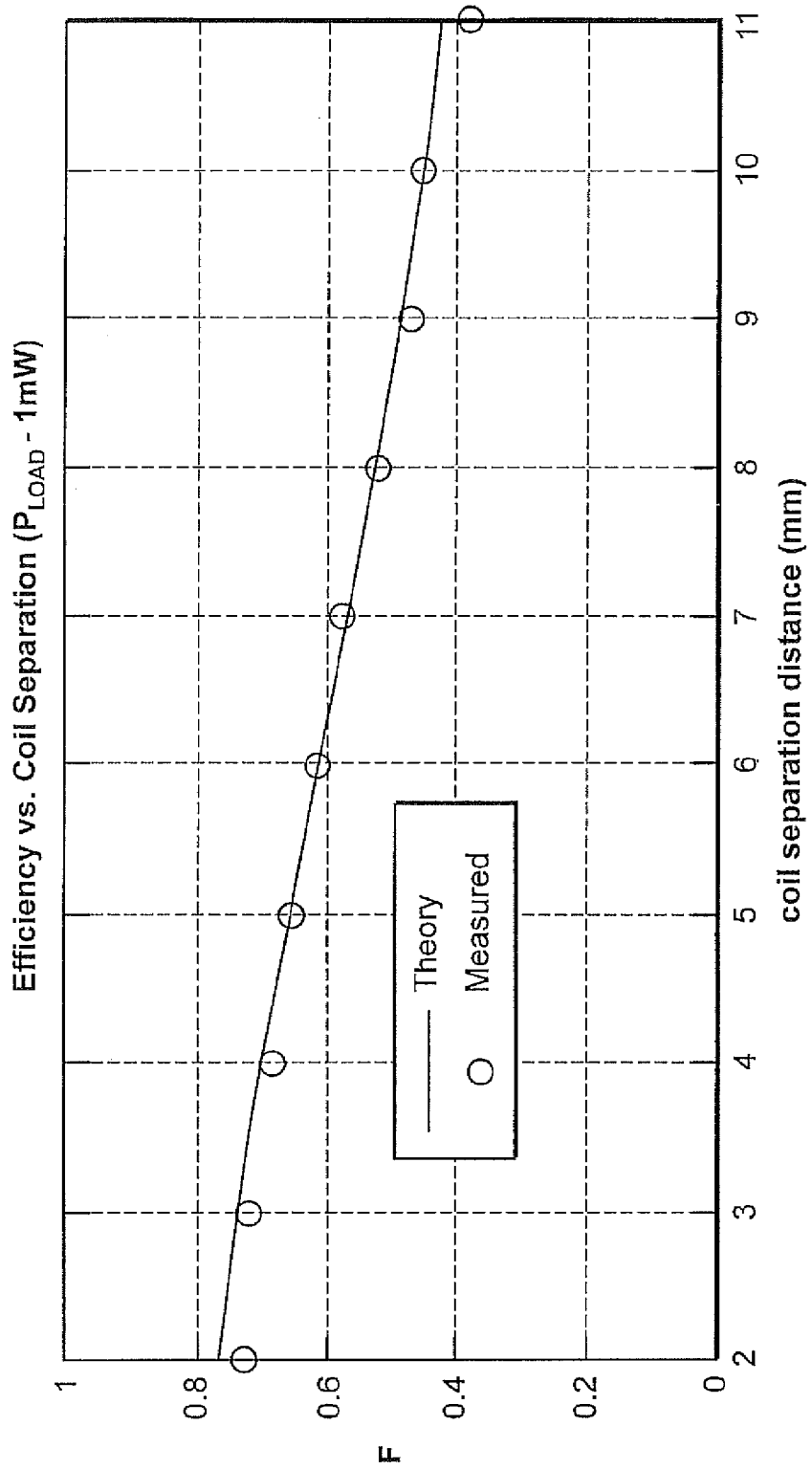
FIG. 6C is a graph demonstrating the theoretical and measured efficiency of the link as a function of distance between primary and secondary coils.

An RF power link system 60 is shown in FIG. 6A. The system 60 uses a custom Class-E driver 66, built on a chip, a primary resonator circuit 62, a secondary resonator circuit 64 and a Schottky diode rectifier D as shown in FIG. 6B. The rectifier D loads the secondary resonator 64 with an effective AC resistance of $R_L/2$ if there is little ripple on the load $R_L$, a necessary condition for a good power supply. Ignoring rectifier D and driver 66 losses, a theoretical analysis shows that the maximum possible power efficiency in the link occurs when the load $R_L$ is chosen so that $Q_L=\omega R_L C_2/2=(1/k)\sqrt{(Q_2/Q_1)}$ and is given by $\eta_{max}=k^2 Q_1 Q_2/((kQ_1+1)(kQ_2+1))$, where k is a geometry-dependent coupling factor and $Q_1$ and $Q_2$ are the quality factors of the primary $L_1$ and secondary $L_2$ resonators, respectively. FIG. 6C shows that theoretical and experimental measurements are in good accord and were taken for $Q_1 \approx 40$ and $Q_2 \approx 70$. RF power links can thus be quite power efficient if operated near their optima.

The invention includes low power implanted DAC-programmable analog circuits that are configured by an external DSP or field-programmable gate array (FPGA). Depending on the user's choice, the system can be configured to report raw neural data from a selected set of electrodes, single and multiunit spikes extracted via spike sorting, local field potential (LFP) data, or decoded motor parameters via a data telemetry 'uplink'. Such flexibility is possible because the parameter values for the analog wavelet-like spike-sorting filters or other analog parameters are determined by detailed digital analysis of raw uplinked analog neural data and then downloaded into the implant via a low-bandwidth telemetry 'downlink.' Since the relatively power-hungry digital analysis need only be done occasionally to keep the system up-to-date as spikes or neurons appear or disappear, the overall power consumption of the system remains low but the flexibility of a digital system can be leveraged.

Figure 7A:
FIG. 7A is a schematic diagram, of the chip-on-board wireless neural stimulation system.
Figure 7A:
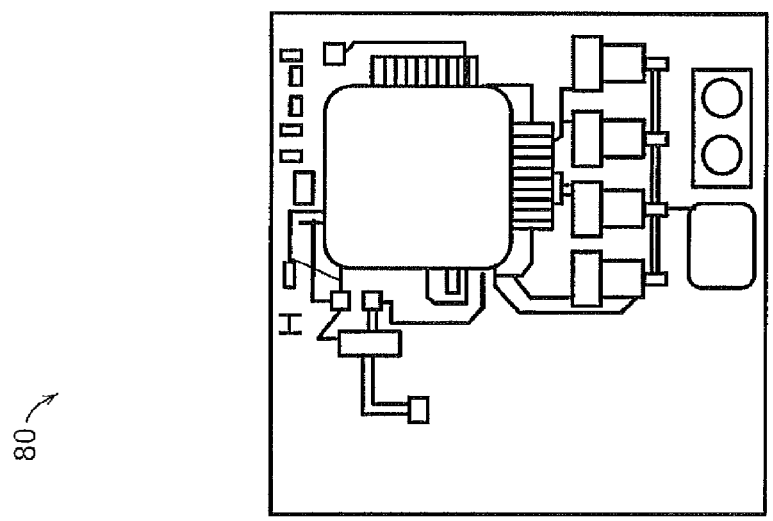

Thus far, circuits and systems were focused on capable only of recording from neurons in the brain. FIG. 7A shows miniature printed circuit board 80 having a receiver coil and electrodes on its reversed side, battery, and a custom integrated circuit for data demodulation and neural stimulation, as shown in FIG. 7C.

Figure 7B:
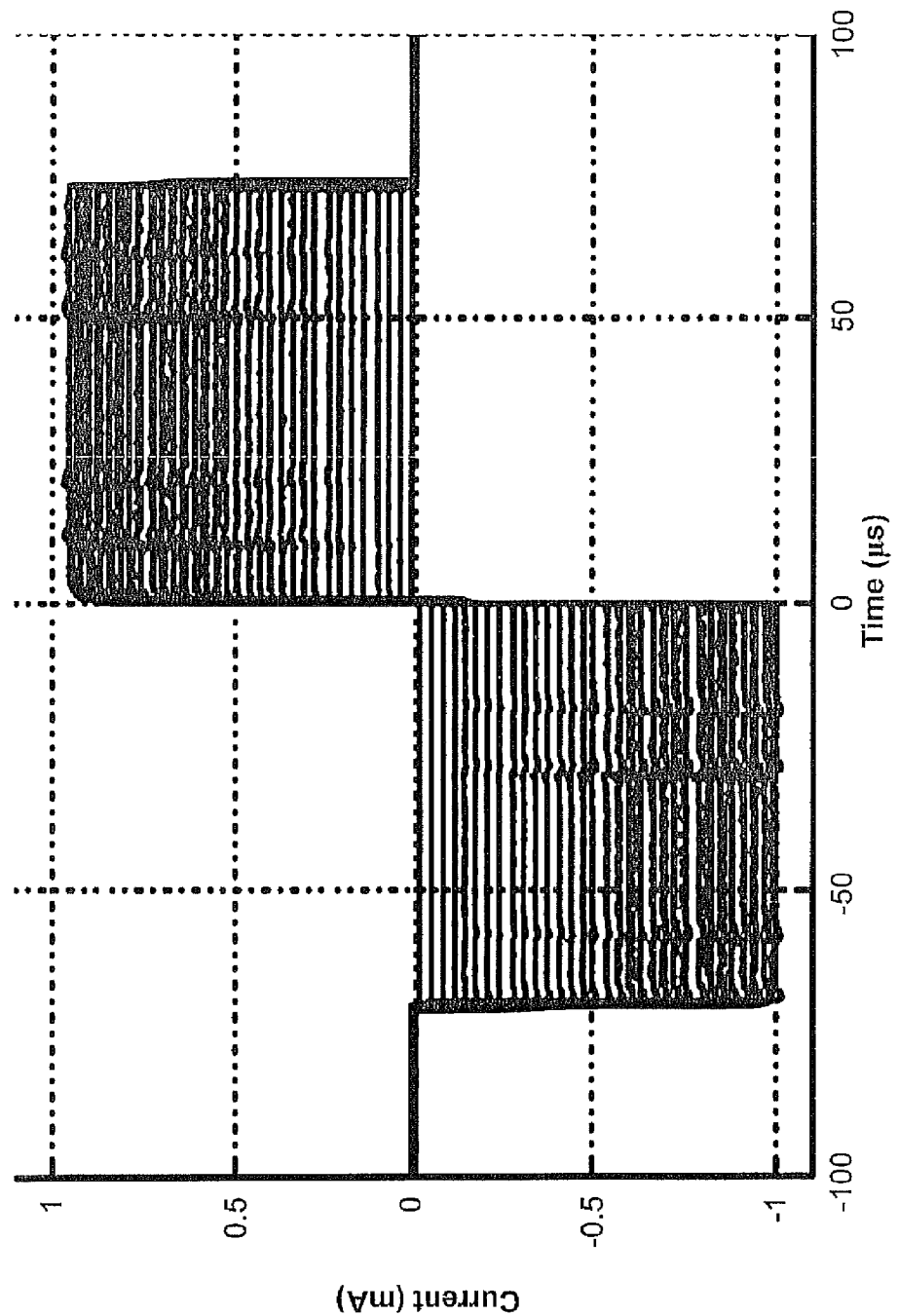
FIG. 7B is a graph demonstrating the measured biphasic current pulses demonstrating 32 stimulation levels.
Figure 7C:
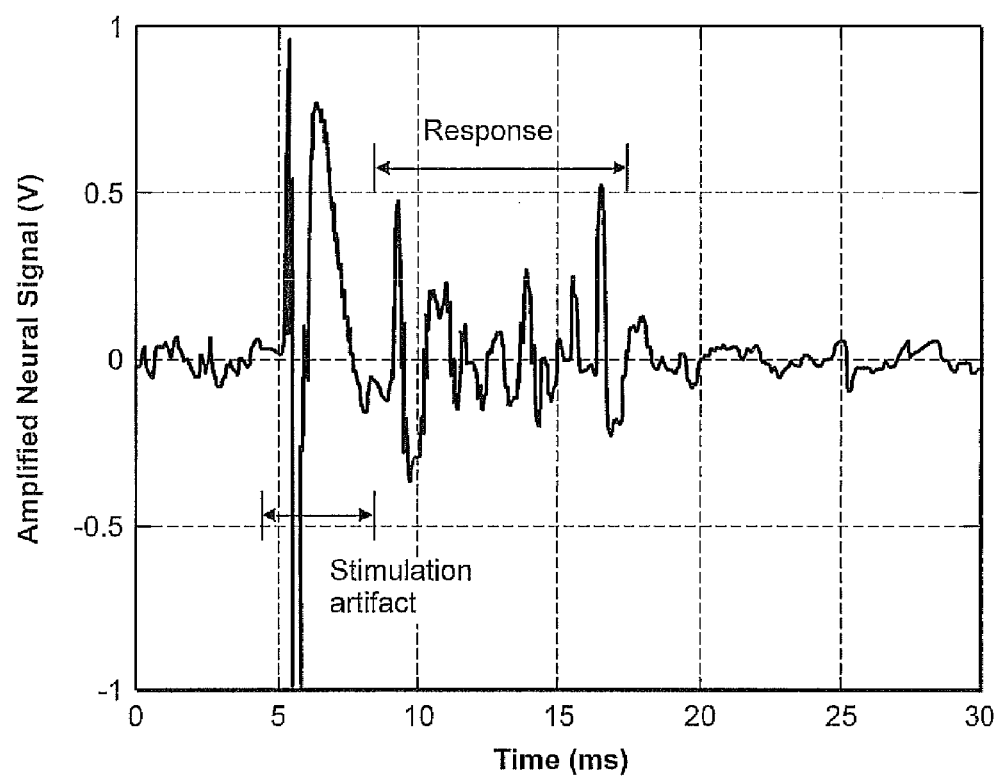
FIG. 7C is a graph demonstrating the HVC (High Vocal Center) response to neural stimulation in an area.

The chip, fabricated in a standard 0.5 µm CMOS process, occupies 2.25 mm$^2$ and is capable of delivering biphasic current pulses to 4 addressable electrode sites at 32 selectable current levels ranging from 10 µA to 1 mA, as shown in FIG. 7B. The entire implant weighs 0.6 g (including battery) and occupies a footprint smaller than 1.5 cm$^2$. During periods of neural inactivity, the chip can automatically enter a sleep mode in which it uses only 7 µA of quiescent current. When neural activity or its behavioral or other correlates (such as birdsong) are detected (for example, by a microphone in the case of the birdsong experiments), a wireless transmitter is automatically activated, and the transmitter generates an RF signal. A detector on board the chip receives this signal and wakes up the data demodulation and output driver circuitry. This system demonstrates the practicability of a power efficient scheme for programmable neural stimulation.

Although the present invention has been shown and described with respect to several preferred embodiments thereof, various changes, omissions and additions to the form and detail thereof, may be made therein, without departing from the spirit and scope of the invention.

What is claimed is:

1. An ultra-low-power microelectronic system for wireless neural recording capable of being completely implanted in the brain, comprising:
   a plurality of neural amplifiers with adaptive power biasing used in multi-electrode arrays, wherein said neural amplifiers comprise a gain stage implemented using an all-subthreshold and folded cascode architecture to allow low-voltage operation and a bandwidth limiting stage to maintain a constant overall bandwidth and to vary a bias current of said gain stage so as to adjust a noise per unit bandwidth of said gain stage;
   an adaptive learning architecture for neural signal decoding that uses a continuous-time analog gradient descent algorithm to learn a decoding filter via supervised learning or other learning techniques that is implantable in a brain;
   an impedance-modulation telemetry system for low-power data telemetry used by a plurality of brain-machine interfaces to transmit RF data from the brain flexibly and efficiently so as to permit power consumption to occur outside a body rather than within the brain;
   a wireless link for efficient power transfer.

2. The system of claim 1 further comprising at least one circuit for wireless stimulation of neurons.

3. The system of claim 1 further comprising an impedance-modulation wireless link in conjunction with a brain-machine interface.

4. The system of claim 3, wherein the link uses near-field inductive coupling between the implanted system and an external transceiver.

5. The system of claim 4, wherein the link is designed to minimize power consumption in the brain-implanted system or support high data rates from the implanted to the external system.

6. The system of claim 1, wherein the analog decoding and learning architecture includes a data compression stage.

7. An ultra-low-power circuit for wireless neural recording and stimulation comprising:
   a neural amplifier with adaptive power biasing for use in multi-electrode arrays, wherein said neural amplifier comprises a gain stage implemented using an all-subthreshold and folded cascode architecture to allow low-voltage operation and a bandwidth limiting stage to maintain a constant overall bandwidth and to vary a bias current of said gain stage so as to adjust a noise per unit bandwidth of said gain stage;
   an adaptive learning architecture for neural signal decoding that uses a continuous-time analog gradient descent algorithm to learn a decoding filter via supervised learning or other learning techniques that is implantable in a brain;
   an impedance-modulation telemetry system for low-power data telemetry used by a plurality of brain-machine interfaces to transmit RF data from the brain flexibly and efficiently so as to permit power consumption to occur outside a body rather than within the brain;
   a wireless link for efficient power transfer; and
   at least one circuit for wireless stimulation of neurons.

8. The ultra-low-power circuit of claim 7, wherein said impedance-modulation telemetry system further comprises:
   an external unit broadcasting a continuous wave carrier using a class-E amplifier topology; and
   an implanted unit that switches its impedance from minimum, a series resonant coil, to a maximum, an open-circuited coil by using a switch in series with a capacitor to amplitude modulate a load at the external unit.

9. The ultra-low-power circuit of claim 7, wherein said ultra-low-power circuit saves power by entering into a sleep mode during inactivity, and is activated upon receiving a pre-determined signal.

10. The ultra-low-power circuit of claim 7, wherein said ultra-low-power circuit is implemented as a hybrid analog-digital architecture using DAC-programmable analog circuits that are configurable via an external digital signal processor.

11. The ultra-low-power circuit of claim 7, wherein said ultra-low-power circuit is usable in conjunction with a neuromotor prosthetic system.

12. An ultra-low-power circuit for wireless neural recording and stimulation comprising:
   a neural amplifier with adaptive power biasing for use in multi-electrode arrays, said neural amplifier having a gain stage implemented using an all-subthreshold and folded-cascode architecture to allow low-voltage operation and a bandwidth limiting stage to maintain a constant overall bandwidth and to vary a bias current of said gain stage so as to adjust noise per unit bandwidth of said gain stage;
   an adaptive learning architecture for data compression, said adaptive learning architecture implemented using a gradient descent algorithm to learn a decoding filter via supervised learning or other learning techniques that is implantable in a brain;
   an impedance-modulation telemetry system for low-power data telemetry, said impedance-modulation telemetry system comprising an external unit broadcasting a continuous wave carrier using a class-E amplifier topology; and an implanted unit that switches its impedance from minimum, a series resonant coil, to a maximum, an open-circuited coil by using a switch in series with a capacitor to amplitude modulate a load at the external unit, said impedance-modulation telemetry system allows a plurality of brain-machine interfaces to transmit RF data from the brain flexibly and efficiently so as to permit power consumption to occur outside a body rather than within the brain;

a wireless link for efficient power transfer; and at least one circuit for wireless stimulation of neurons.

13. The ultra-low-power circuit of claim 12, wherein said ultra-low-power circuit saves power by entering into a sleep mode during inactivity, and is activated upon receiving a pre-determined signal.

14. The ultra-low-power circuit of claim 12, wherein said ultra-low-power circuit is implemented as a hybrid analog-digital architecture using programmable circuits that are configurable via an external processor; including, as one instantiation, a hybrid analog-digital architecture using DAC-programmable analog circuits configurable via an external digital signal processor.

15. The ultra-low-power circuit of claim 12, wherein said ultra-low-power circuit is usableused in conjunction with a neuromotor prosthetic system.

16. A method of implementing an ultra-low-power circuit for wireless neural recording and stimulation comprising:

providing a micropower neural amplifier with adaptive power biasing for use in multi-electrode arrays, wherein said micropower neural amplifier comprises a gain stage implemented using an all-subthreshold and folded cascode architecture to allow low-voltage operation and a bandwidth limiting stage to maintain a constant overall bandwidth and to vary a bias current of said gain stage so as to adjust a noise per unit bandwidth of said gain stage;

providing an adaptive learning architecture for data compression, said adaptive learning architecture uses a continuous-time analog gradient descent algorithm to learn a decoding filter via supervised learning or other learning techniques that is implantable in a brain;

providing an impedance-modulation telemetry system for low-power data telemetry, said impedance-modulation telemetry system allows a plurality of brain-machine interfaces to transmit RF data from the brain flexibly and efficiently so as to permit power consumption to occur outside a body rather than within the brain;

providing a wireless link for efficient power transfer; and providing at least one circuit for wireless stimulation of neurons.

17. The method of claim 16, wherein said impedance-modulation telemetry system further comprises:

an external unit broadcasting a continuous wave carrier using a class-E amplifier topology; and an implanted unit that switches its impedance from minimum, a series resonant coil, to a maximum, an open-circuited coil by using a switch in series with a capacitor to amplitude modulate a load at the external unit.

18. The method of claim 16, wherein said ultra-low-power circuit saves power by entering into a sleep mode during inactivity, and is activated upon receiving a pre-determined signal.

19. The method of claim 16, wherein said ultra-low-power circuit is implemented as a hybrid analog-digital architecture using programmable circuits that are configurable via an external processor; including, as one instantiation, a hybrid analog-digital architecture using DAC-programmable analog circuits configurable via an external digital signal processor.

20. The method of claim 16, wherein said ultra-low-power circuit is usable in conjunction with a neuromotor prosthetic system.

21. A method of performing the operations of an ultra-low-power circuit for wireless neural recording and stimulation comprising:

performing adaptive power biasing for use in multi-electrode arrays, said neural amplifier having a gain stage implemented using an all-subthreshold and folded-cascode architecture to allow low-voltage operation and a bandwidth limiting stage to maintain a constant overall bandwidth and to vary a bias current of said gain stage so as to adjust a noise per unit bandwidth of said gain stage;

compressing data using a gradient descent algorithm to learn a decoding filter via supervised learning or other learning techniques that is implantable in a brain;

performing low-power data telemetry using a impedance-modulation telemetry system comprising an external unit broadcasting a continuous wave carrier using a class-E amplifier topology; and an implanted unit that switches its impedance from minimum, a series resonant coil, to a maximum, an open-circuited coil by using a switch in series with a capacitor to amplitude modulate a load at the external unit, said impedance-modulation telemetry system allows a plurality of brain-machine interfaces to transmit RF data from the brain flexibly and efficiently so as to permit power consumption to occur outside a body rather than within the brain;

transferring power using wireless link; and wirelessly stimulating neurons.

22. The method of claim 21 further comprising saving power by entering into a sleep mode during inactivity, and is activated upon receiving a pre-determined signal.

23. The method of claim 21 further comprising providing a hybrid analog-digital architecture using programmable circuits that are configurable via an external processor; including, as one instantiation, a hybrid analog-digital architecture using DAC-programmable analog circuits configurable via an external digital signal processor.

24. The method of claim 21, wherein said ultra-low-power circuit is used in conjunction with a neuromotor prosthetic system.

* * * * *